United States Patent
Curtis

(10) Patent No.: US 9,827,151 B1
(45) Date of Patent: Nov. 28, 2017

(54) UNITARY DISPOSABLE DIAPER WITH INTEGRATED SOILAGE-MANAGEMENT STRUCTURE INCLUDING DISPOSAL CONTAINER

(71) Applicant: Jamie Lee Curtis, Santa Monica, CA (US)

(72) Inventor: Jamie Lee Curtis, Santa Monica, CA (US)

(*) Notice: Subject to any disclaimer, the term of this patent is extended or adjusted under 35 U.S.C. 154(b) by 0 days.

(21) Appl. No.: 15/258,984

(22) Filed: Sep. 7, 2016

(51) Int. Cl.
| A61F 13/551 | (2006.01) |
| A61F 13/84 | (2006.01) |
| A61F 13/49 | (2006.01) |
| A61F 13/496 | (2006.01) |

(52) U.S. Cl.
CPC ............ *A61F 13/84* (2013.01); *A61F 13/496* (2013.01); *A61F 13/49017* (2013.01); *A61F 13/5512* (2013.01); *A61F 13/5519* (2013.01); *A61F 2013/55125* (2013.01); *A61F 2013/8402* (2013.01)

(58) Field of Classification Search
CPC .............. A61F 13/551; A61F 13/55105; A61F 13/5512; A61F 13/5519; A61F 2013/55125; A61F 2013/55195; A61F 2013/8402
See application file for complete search history.

(56) References Cited

U.S. PATENT DOCUMENTS

| 4,221,221 | A | | 9/1980 | Ehrlich | |
| 4,417,894 | A | | 11/1983 | Norris | |
| 4,604,096 | A | * | 8/1986 | Dean | A61F 13/551 604/385.13 |
| 4,753,647 | A | | 6/1988 | Curtis | |
| 4,808,175 | A | * | 2/1989 | Hansen | A61F 13/551 383/63 |
| 4,964,859 | A | * | 10/1990 | Feldman | A61F 13/551 206/223 |
| 7,569,038 | B1 | * | 8/2009 | Salem, Jr. | A61F 13/15252 604/385.01 |
| 2004/0092901 | A1 | * | 5/2004 | Reece | A61F 13/84 604/385.06 |
| 2005/0256487 | A1 | * | 11/2005 | Williams | A61F 13/551 604/385.19 |
| 2005/0267432 | A1 | * | 12/2005 | Sundberg | A61F 13/551 604/385.13 |
| 2009/0326501 | A1 | * | 12/2009 | Foley | A61F 13/551 604/385.06 |
| 2011/0125123 | A1 | * | 5/2011 | Moriji | A61F 13/5512 604/385.13 |

* cited by examiner

*Primary Examiner* — Lynne Anderson
(74) *Attorney, Agent, or Firm* — Kolisch Hartwell, P.C.

(57) ABSTRACT

A unitary, disposable diaper possessing integrated soilage-management structure including a portion structured to form a selectively deployable, ultimately closable and sealable, soilage-impervious disposal container which enables after-baby-clean-up discarding of the entire, integrated, soiled diaper componentry as a compact disposable unit.

2 Claims, 4 Drawing Sheets

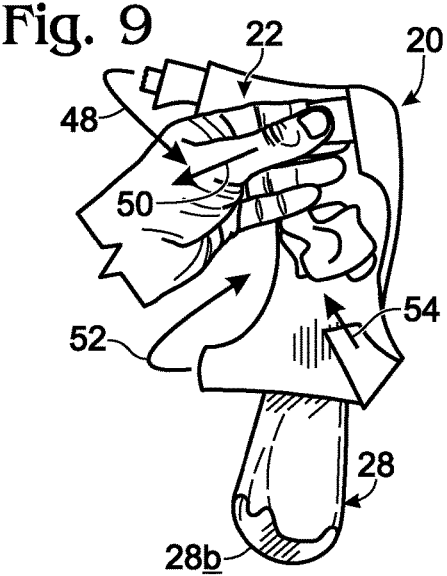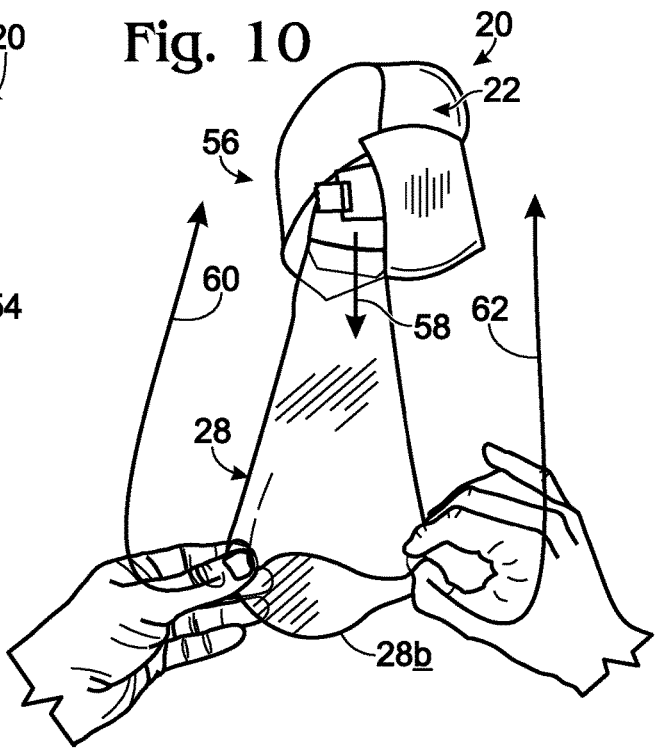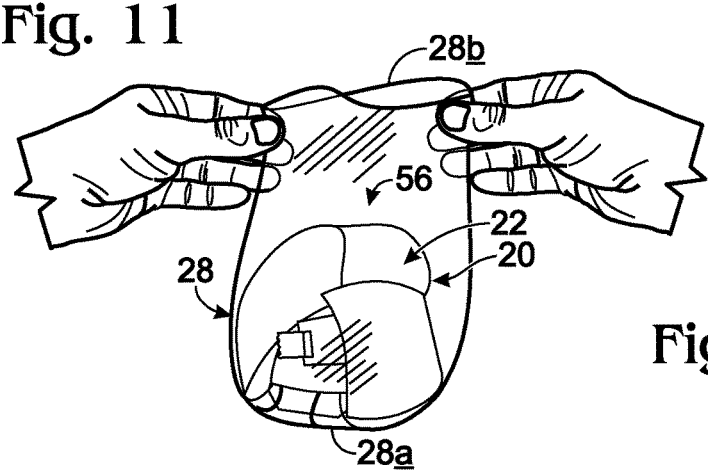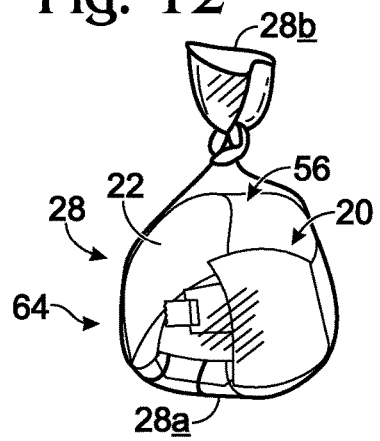

UNITARY DISPOSABLE DIAPER WITH INTEGRATED SOILAGE-MANAGEMENT STRUCTURE INCLUDING DISPOSAL CONTAINER

BACKGROUND AND SUMMARY OF THE INVENTION

This invention pertains to a unitary, disposable, baby diaper, and in particular to such a diaper which possesses, in a manner integrated with its main body structure, unique soilage-management structure that includes, in accordance with an important feature of the invention, a portion designed as a selectively deployable, diaper-main-body-attached and unitized, ultimately (i.e., at the conclusion of a diaper-changing procedure after removal of a soiled diaper from a baby) closeable and sealable, soilage-impervious disposal container, or disposal-container structure. According to this special feature of the invention, the proposed disposal container/container structure, which preferably takes the form of a lightweight plastic bag, and which is initially stored compactly in a flap-closed pocket that forms part of the soilage-management structure, is usable, after soiled-diaper removal from a baby, to receive, in their entireties, all of the soiled components of the removed diaper in preparation for easy, cleanly handleable, and convenient disposal/discard of these components as a single, compact, disposable unit. The terms "soilage" and "soiled", and the like, employed herein refer to both urine and feces.

Preferably, although, and this at the free choice/option of the invention practicer, not necessarily, included also in the pocket of the soilage-management structure of the invention is at least one, and preferably more than one, such as perhaps three, conventional clean-up wipers (also referred to herein as wipes).

As will become very apparent from the full description of this invention as such is set forth below herein, the invention proposes, in all modifications thereof, an extremely high-utility, "all-in-one", readied-for-baby-cleaning, and for soiled-diaper-component disposal, arrangement which offers a strikingly appealing improvement in the world of disposable diaper construction and post-soilage handling.

This invention is thus offered in relation to easing a long-standing routine which is repetitively familiar to parents and caregivers of infants everywhere—a routine which involves infant, soiled-diaper clean-up, along with subsequent handling and discarding of soiled, disposable diapers. Considering, by way of background, certain earlier and related convenience-promoting advances in diaper construction, U.S. Pat. No. 4,753,647, which issued to me in June of 1988, illustrates, describes and covers a disposable diaper that includes, as a significant, then-offered improvement, an outer, soilage-protected, soilage-impervious pocket joined to the main body of a diaper and containing one or more clean-up wipes. This earlier improvement, which I created some time ago, offers an important post-use, i.e. soiled-diaper-management, convenience for performing infant clean-up by establishing a setting wherein the diaper-included one or more clean-up wipes are thus readily at hand—not requiring that a parent, etc. regularly have on hand for home use, or with a need to transport when away from home, two categories of diaper-related packaging—one containing disposable diapers, per se, and the other holding clean-up wipes.

In the interest of aiding, as appropriate, an understanding of, and the background for, the special, new contributions made to the disposable-diaper art by the present invention, the entire disclosure content of above-identified U.S. Pat. No. 4,753,647 is hereby incorporated herein by reference.

Augmenting the disposable-diaper improvement made by the invention described in the '647 patent, the present invention, as will become understood, offers yet other important improvements in unitary disposable-diaper construction and utility.

A key contribution to the disposable diaper art made by the present invention, as has been suggested above, involves the integration, with the main body structure of a disposable infant diaper, of soilage-management structure which features, among other things, what is referred to herein as a selectively deployable, main-body-unitized, sealable and soilage-impervious disposal-container structure. This container structure preferably takes the form of a compact, deployable, ultimately closeable and sealable, soilage-impervious bag, or bag structure, such as a lightweight plastic bag made of any suitable, conventional, lightweight plastic material. Such a bag is initially compactly folded and stored in, for ultimate, selective, pre-use deployment from, a soilage-impervious, flap-closed pouch, or pocket, formed on the outer, front side of the main body of a diaper constructed according to the invention. This bag has its normally closed end suitably attached, or affixed and unitized, solely to the diaper's main body structure at but a single attachment point, or location, which is disposed directly adjacent the openable end of the pocket, or pouch, this openable end also being referred to herein as an upper-end exposure opening for the pocket, which opening accommodates access to the inside of the pocket.

Additionally, the soilage-management structure of the invention preferably, although not necessarily, also includes, initially stored for ultimate use removal, and in the same pocket, or pouch, just mentioned, at least one, and preferably a plurality, say about three, clean-up wipes.

In relation to the background, and proposed new features, settings that have just generally been set forth, and to clarify how the special contributions of the present invention stand out from conventionality, it should be understood that, in the world today of available, disposable diapers, there are many manufactured styles of such diapers—both in terms of materials selected for construction, as well as in terms of chosen internal organizations of these materials. The present invention does not involve basic, main-body, etc., diaper construction, or any of such main-body particular features. Rather, the newly invented contributions made by the present invention contemplate additional, newly introduced diaper features which may be incorporated, in an integrated fashion, and very readily in the current constructions of otherwise conventional diaper-body structures. These conventional structures will, of course, typically be formed with appropriate soilage-capturing and soilage-leakage-control considerations.

Accordingly, no part of the present invention relies in any way upon revisions in conventional disposable-diaper main-body construction. The invention does, however, rely upon those aspects of conventional diaper-main-body materials selection and construction which assure that urine and feces discharge from an infant which soils the inside of a diaper does not, and cannot, leak to the outside surface expanse, and particularly to the frontal outside surface expanse, of the diaper's main body, per se, where components of the invention's proposed soilage-management structure are intended to be located.

With the above thoughts in mind, from one high-level point of view, the present invention can be characterized as a unitary, disposable diaper possessing integrated soilage-management structure including a deployable portion structured to form a closable and sealable, soilage-impervious disposal container, or disposal-container structure. The soilage-management structure preferably may also include at least one clean-up wiper, or wipe.

From another point of view, the invention may be described as a unitary, disposable diaper which includes a main body structure, and integrated therewith, and protected, in a pre-employed (i.e., pre-soilage, pre-use condition), against inadvertent soilage, sealable disposal-container structure employable, under a circumstance with the diaper and any associated structure soiled, to receive and seal the soiled structure as a whole in a contained and sealed condition readied for discard as a disposable unit. In a more detailed expression of the invention in this vein, the diaper's main body structure has an outer front side on which the soilage-management structure is suitably disposed, with certain of its components initially stored in a closed, but readily openable, soilage-impervious pouch, pocket, or pocket structure. The disposal container, or disposal-container structure, is affixed just to the main body structure of the diaper, and at an affixation location which is directly adjacent the openable end of the mentioned pocket/pouch. This container is preferably a readily compactible soilage-impervious bag formed of a suitable, lightweight plastic material. Additionally, and as has been mentioned above, the soilage-management structure may, and preferably does, include at least one clean-up wipe, and as a practical matter, since more than one such wipe is usually needed, I suggest that about three wipes be included—this, of course, being up to the wishes of the invention practicer.

Still another way of viewing the invention is that it features a unitary, disposable diaper having a main body structure, and integrated with this body structure, soilage-management structure, protected, in a pre-use condition, against inadvertent soilage, and including at least one clean-up wiper, and sealable disposal-container structure which is employable, under a circumstance with components of the diaper, including the at least one wiper, soiled, to receive and seal such components as a whole in a contained and sealed condition readied for discard as a disposable unit.

Yet a further way of expressing the invention, in relation to one of its possible embodiments, is that it takes the form of a unitary, disposable diaper possessing (a) a main body structure, or body, having an outer side with a front portion, (b) an initially and nominally flap-closed, but selectively openable, soilage-impervious storage pocket structure, or pocket, formed on the diaper body's outer side's front portion, having an openable, upper-end exposure opening, and an inside structured to be protected initially against any soilage incursion, and (c), initially stored within this pocket structure, (1) at least one clean-up wiper, and (2) a sealable, soilage-impervious, main-body-attached and unitized, disposal-container structure anchored just to the diaper's main body structure at the location of the just mentioned exposure opening of the storage pocket, and employable, under a circumstance with the main body structure and any other components of the diaper, including the at least one wiper, soiled, to receive all of the soiled structure and seal it in a contained condition readied for disposal.

These and other features and advantages of, and offered by, the unitary, disposable integrated-componentry diaper of the present invention will become more readily apparent as the detailed description of it which is set forth below is read in conjunction with the accompanying drawings.

DESCRIPTIONS OF THE DRAWINGS

Figure 1:
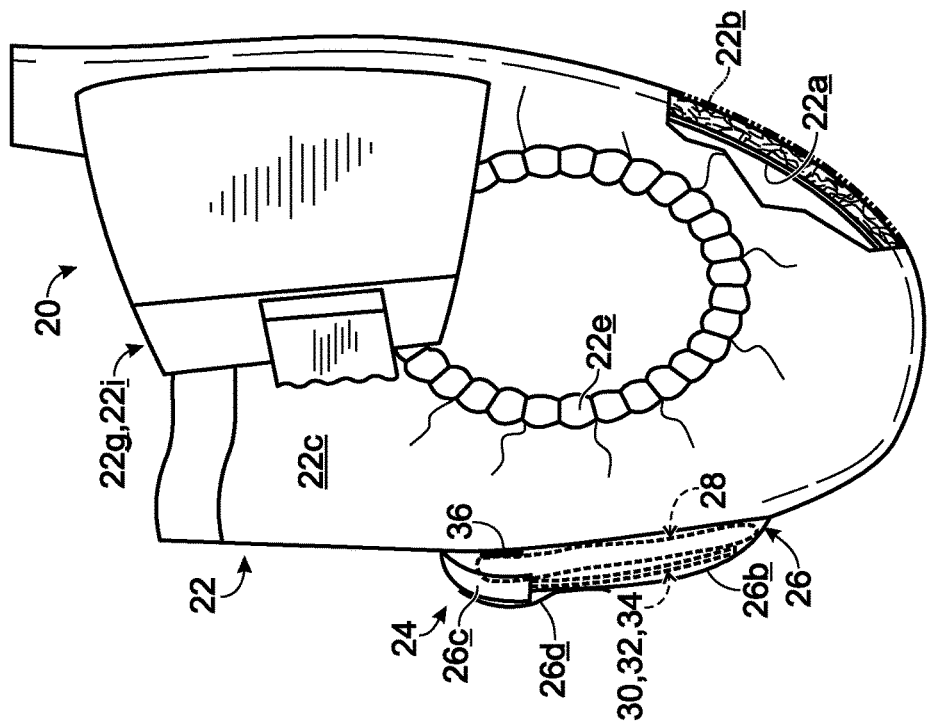
FIG. 1 is a front view of a unitary disposable diaper possessing integrated soilage-management structure constructed in accordance with a preferred embodiment of the present invention.
Figure 2:
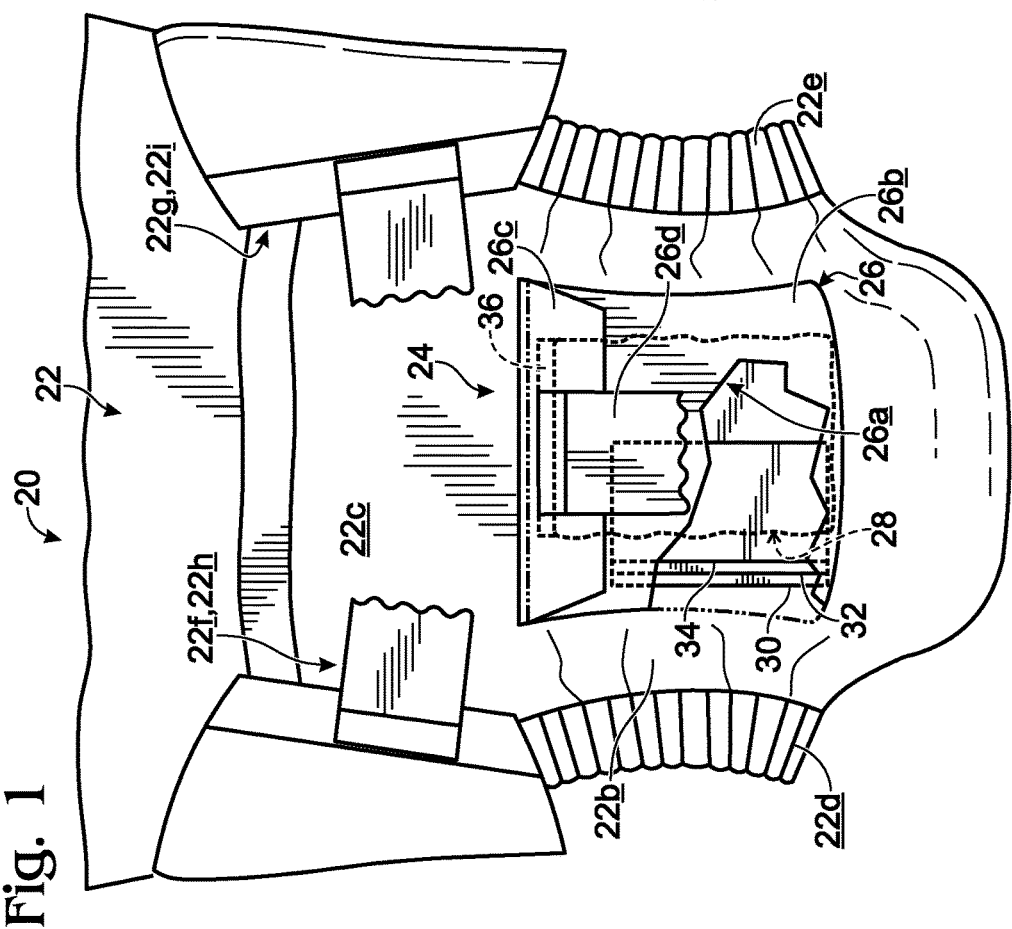
FIG. 2 is a side elevation of the diaper of FIG. 1, taken from the right side of, and drawn on the same scale as, FIG. 1.

In FIGS. 1 and 2, the diaper there pictured is shown in what may be thought of as a closed condition, as if fitted to a baby.

Figure 3:
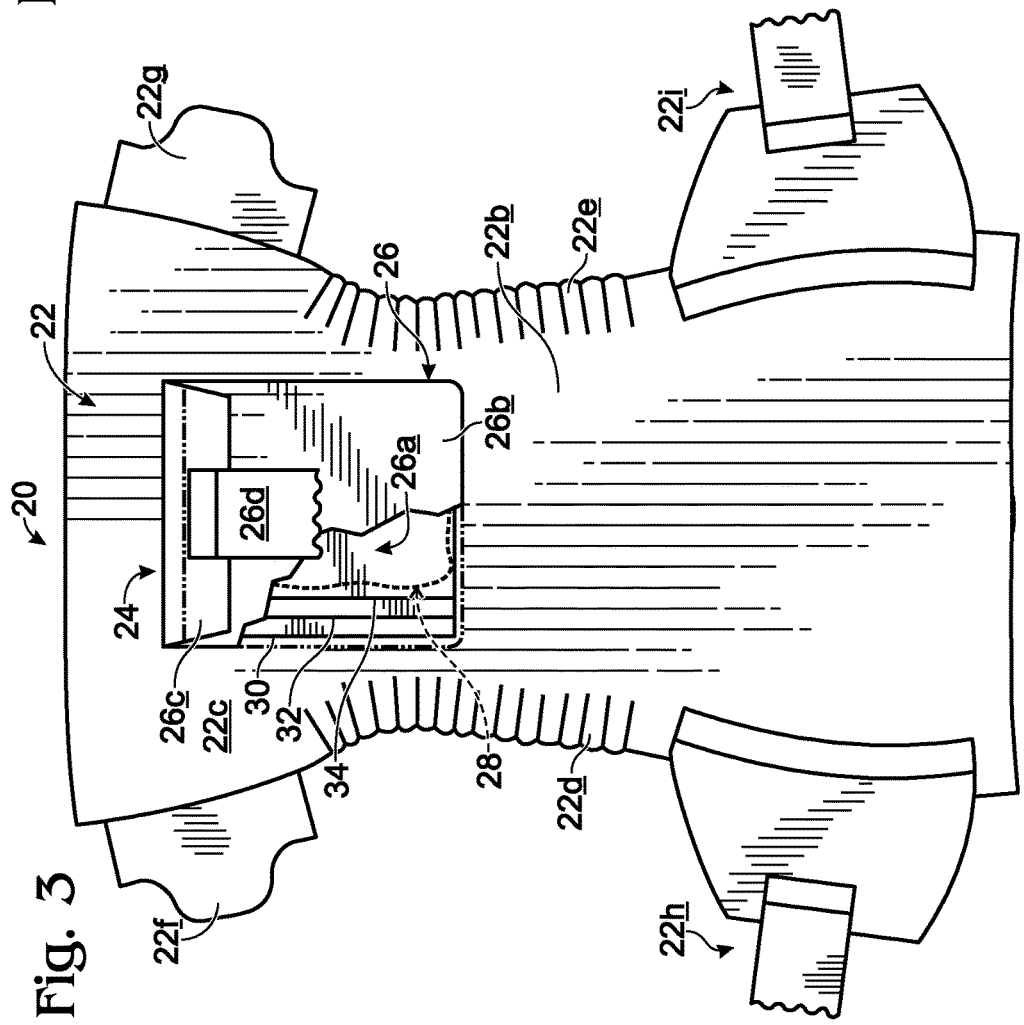

FIG. 3, which is drawn on a smaller scale than that employed in FIGS. 1 and 2, presents an outer-side plan view of the main body, or main body structure, of the diaper of FIGS. 1 and 2. In particular, in FIG. 3, the diaper's main body is pictured laid out flat, with its front portion disposed toward the upper part of FIG. 3.

In FIGS. 1-3, inclusive, certain portions of diaper structure are broken away both to reveal details of construction, and to highlight the presences of various included components.

Figure 4:
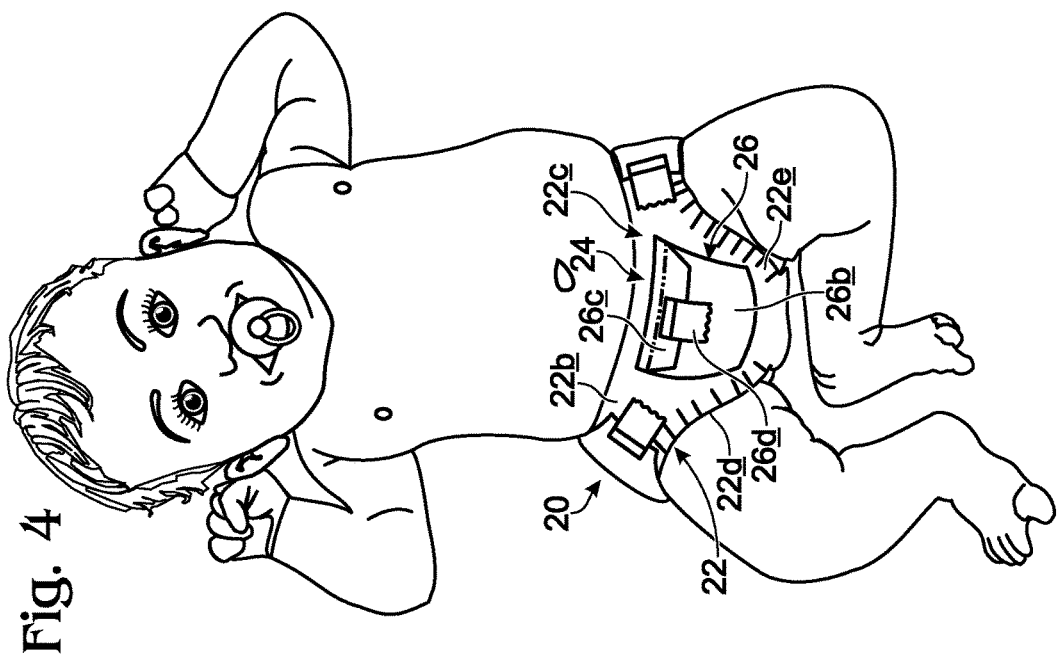

FIG. 4 is a yet smaller-scale view illustrating the diaper of FIGS. 1-3, inclusive, in a condition being worn by an infant.

FIGS. 5-12, inclusive, each of which is drawn on a common scale that is like the scale employed in FIG. 4, and each of which is described in more detail immediately below, collectively show, in numeric-figure order, images describing several stages in a typical use-sequence involving the diaper of the invention.

Figure 5:
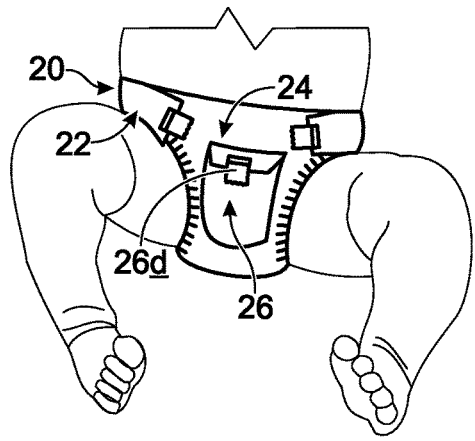

FIG. 5 is a fragmentary, frontal view showing a baby wearing a soiled diaper constructed in accordance with the present invention ready for removal and disposal.

FIGS. 1-5, inclusive, each illustrates both (a) what is referred to herein as a pre-diaper-change condition of the invented diaper, and also (b) what is called a state of nominal closure of an exposure opening that is provided for the storage pocket structure which is included in the diaper.

Figure 6:
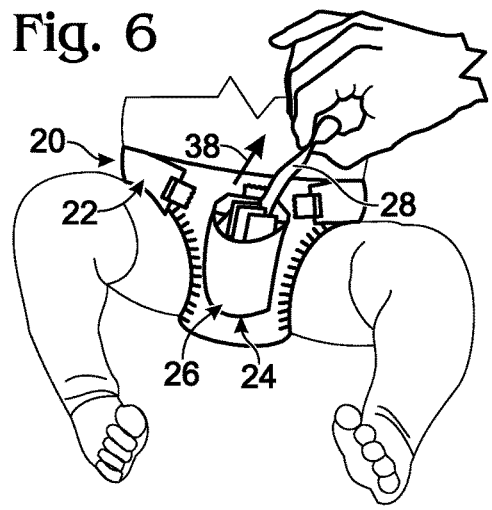

FIG. 6 illustrates an early result of closure-flap manipulation-opening of a soilage-impervious pocket, or pocket structure, which forms part of diaper-body-integrated soilage-management structure included in the present invention. In particular, this figure pictures, preliminarily, the act of deploying an included bag/container structure (which has been stored in the pocket structure) in preparation for using this bag structure to receive, and to seal as by knotting its initially open end, for disposal within it as a singular, disposable unit, all soiled diaper components as a completion part of the process of changing the diaper for the baby.

Figure 7:
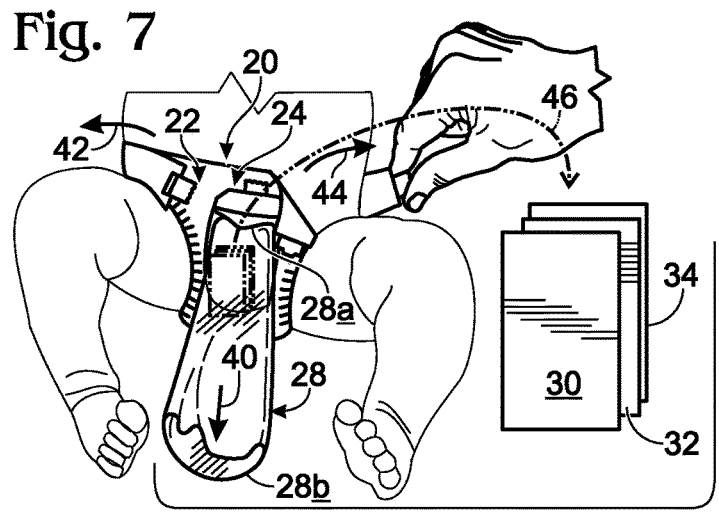

FIG. 7 shows a later stage in the overall clean-up and soiled-diaper-changing process, wherein (1) pocket-contained clean-up wipes (three in representative number in the diaper structure pictured herein) have been removed from the pocket, (2) the attached disposal bag structure has been outwardly drawn, away from the diaper's main body structure, and initially deployed—its permanently closed end remaining attached to the main body structure—with its open end exposed, and facing the viewer in this figure, in readiness (as is described shortly below with reference to what is shown in FIG. 10) for use in relation to soiled diaper-componentry collection, containment and disposal, and (3) the soiled diaper is being taken off the baby. The diaper-body-attached, normally closed end of the bag structure (hidden in this view) is, and remains, as mentioned above, attached to the diaper's main body structure directly adjacent the upper-end exposure-opening of the pocket.

Figure 8:
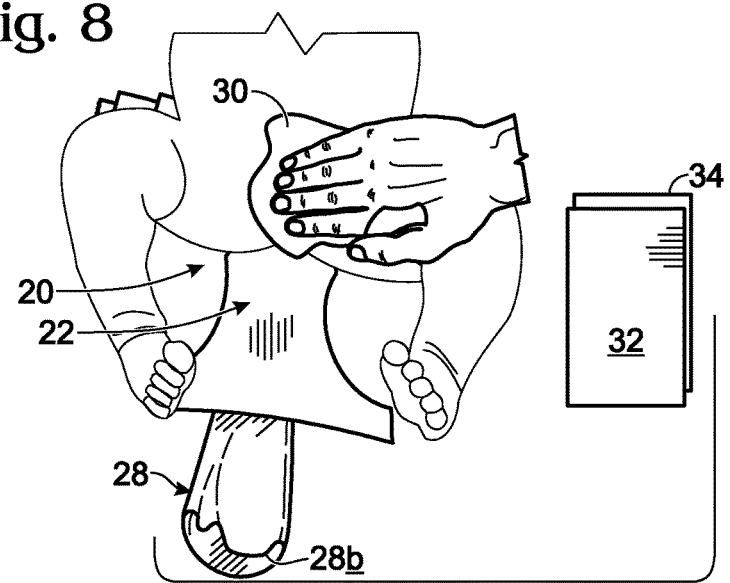

FIG. 8 shows the diaper completely opened, and an initial one of the clean-up wipes being used to clean the baby.

FIG. 9 is drawn with the assumption that the baby (not shown in either this or any of the remaining (and still-to-be-generally discussed) drawing figures) has now been re-diapered, and pictures the now removed, soiled diaper, along with the used wipes, placed all together and being folded ultimately into a tight, compact, disposable "ball", readied for pre-disposal insertion into the diaper-body-attached, disposal bag structure.

FIG. 10 shows the exposed, outer, open end of the deployed, attached disposal bag structure being fully opened up in preparation for the bag structure being turned inside out (as indicated by a pair of laterally spaced, curved arrows) in a condition configured for receiving, and ultimately confining and sealing for clean disposal handling, all of the soiled components (main body and wipes) of the just-removed diaper.

FIG. 11 shows the diaper and all associated soiled components now contained completely inside the disposal bag/container structure, in preparation for what is shown in FIG. 12.

FIG. 12 pictures the disposal bag/container structure knotted (and thereby sealed) and thus readied for disposal/discard as a singular disposable unit which collectively, fully and cleanly (for disposal handling purposes), contains all of the diaper-associated, soiled components.

DETAILED DESCRIPTION OF THE INVENTION

Turning now to the drawings and referring first of all to FIGS. 1-4, inclusive, indicated generally at 20 is a unitary, disposable diaper constructed in accordance with a preferred embodiment of the present invention. Interesting modifications that I consider to be relevant respecting this preferred embodiment are mentioned below at appropriate locations in the following detailed description of the invention, and to some extent, and as will be mentioned, are described and/or are indicated, in one fashion or another, in the drawings.

Diaper 20 includes a main body structure, or body, 22, which is entirely conventional in construction, and, integrated with this body, as will be explained, is what is referred to herein as integrated soilage-management structure 24, certain components in which (still to be described) are collaboratively employable for baby clean-up, and for the subsequent purpose of collecting, in an ultimately compactly sealed and disposable condition, all clean-up and otherwise soiled elements associated with diaper 20 following soiled-diaper changing.

As was mentioned above, specific details of construction, and of materials-selections, regarding diaper main body 22 form no part of the present invention—this body being constructible in any one of a relatively wide variety of currently known and conventional manners for making disposable diapers. As was also mentioned above, the present invention, whose specific, "with-body-integrated", soilage-management componentry confidently relies on such disposable diaper-body conventional construction to provide pre-diaper-change soilage absorbency and containment on the inside of the diaper, and, of course, protection against soilage migration/leakage to the outside of the diaper body.

Diaper body 22, which has a conventional shape (as can be seen pictured in the drawings), includes an inner side 22a, an outer side 22b with a front portion 22c (seen especially well in the upper part of FIG. 3), a pair of elastomeric, side portions 22d, 22e which encircle a baby's legs with the diaper worn, and four, conventional, "contact-operative" (like conventional hook-and-pile attaching structure), quick-attach/quick-release, closure tab structures 22f, 22g, 22h, 22i which function cooperatively, with the diaper in a condition being worn, to secure it in place.

Soilage-management structure 24 is disposed, as can be seen in many of the drawing figures, on the outer side 22b of diaper main body 22, and specifically on front portion 22c of this outer side. Importantly, such placement results in the management structure being conveniently located for access and use during normal diaper changing.

The soilage-management structure, as it is specifically constructed, appointed and formed in the now being described preferred embodiment of the present invention, includes a singular soilage-impervious pocket structure (also referred to as a pocket or pouch) 26, having, as can be seen clearly in FIGS. 1 and 3, a generally rectangular perimetral outline, or boundary. Reference numerals 26a, 26b, 26c, and their associated drawing lead lines, as will now be described in detail, designate various structural aspects and components that make up pocket 26, with numeral 26a and its associated lead line (which is arrow-headed) functioning herein to designate two of such aspects.

Specifically, numeral 26a, in its dual-identification-functioning role herein, designates both (a) the component-storage-intended inside, or inside space, of pocket 26, and as well, (b), a generally rectangular region existing in, and as a part of, the front portion 22c of the outer side part 22b of diaper main body 22. This front-portion region (as considered at 26a), has, as can be seen, a generally rectangular perimetral configuration, or outline, possessing evident (see particularly FIGS. 1 and 3) elongate sides (upper, lower and lateral—not specifically labeled) that make this region substantially coextensive with the perimetral outline of pocket 26. Region 26a forms the inner, rear side of pocket 26.

Considering the other designating role played by reference character 26a, the overall inside of pocket 26 is defined by space 26a which, as can be seen, is the space existing between front-portion region 26a and a facially confronting, independent-component, continuous, spaced front panel 26b which forms part of pocket 26, and whose perimetral boundary (i.e., its four edges) essentially defines, and is thus, by definition, coextensive with, the perimetral boundary mentioned above of pocket 26. The clearly illustrated but not specifically reference-numeral-labeled, elongate lateral edges, and the elongate base, or base edge, (the lower edge) of panel 26b, are bonded/joined to diaper-body portion 22c in any appropriate and conventional manner.

As can be seen particularly well in FIGS. 1, 3 and 4, panel component 26b is continuous between its four edges. Collaboratively, the upper, elongate, free (i.e., not bonded to the front portion 22c of the diaper main body) edge of panel 26b, and the immediately underlying, confronting and spaced elongate stretch of the upper side of region 26a, form an elongate pocket opening, or openable end, at the upper end of pocket 26. This opening, which is also referred to herein both as an upper open end, and as an upper-end exposure opening, for the pocket, and which has, for access convenience, a width, or length, that is substantially the full width, or lateral dimension, of the pocket, as such width is effectively defined by the width of panel 26b—accommodates access to the pocket's inside relative to storage therein, as will shortly be explained, of other components that also make up parts of soilage-management structure 24. As is illustrated clearly in FIGS. 1-4, inclusive, this opening is nominally, i.e., before the occurrence of a soiled-diaper changing procedure, closed by a panel-overlapping, single, elongate and slender, independent-component, substantially full-pocket-width closure flap 26*c* which forms part of the pocket structure. Flap 26*c*, along its upper elongate edge, as such is pictured in the just-mentioned four drawing figures, is suitably conventionally bonded to diaper body portion 22*c*, with such bonding existing generally along a horizontal line closely paralleling, and disposed slightly above, the free upper edge of panel 26*b*.

Appropriately connected to panel 26*b* and flap 26*c*, at the location shown in FIGS. 1-4, inclusive, and further forming a part of pocket structure 26, are the components of a conventional, contact-operative, quick-attach/quick-release structure 26*d*, which is (preferably) much like that provided conventionally in diaper body 22 for previously mentioned tab structures 22*f*, 22*g*, 22*h*, 22*i*.

In accordance with the preferred embodiment of the present invention now being described, initially stored (i.e., in a ready-to-use situation leading up to the completion of a diaper-change procedure) in the inside of pocket 26 are (1) a main-body-attached and unitized, lightweight, and very thinly and compactly folded, soilage-impervious disposal bag structure, or bag, 28, and (2) a plurality (preferably) of conventional baby clean-up wipes 30, 32, 34. Bag 28, certain details about which are discussed later herein, constitutes a portion of the soilage-management structure, and is appropriately deployable, at the conclusion of a diaper-change procedure, to be employed as a fully closeable and sealable, soilage-impervious disposal container for holding all soiled diaper-associated materials for disposal as a single disposable unit.

Regarding the illustrated storage and availability of the mentioned clean-up wipes, it should be understood that, while three such wipes are described herein as being so stored for eventual clean-up use—this number of wipes having been determined through experience to define a reliably good pre-storage count of wipes—it is preferable that at least one such wipe be so stored. Different numbers of stored wipes may, of course, be determined to be included to suit particular invention-practice judgements.

The particular order in which the disposal container bag and the at least one wipe, or the plural wipes (if that is the case), are stored/arranged within pocket 26 is not critical. It is purely a matter of the invention practicer's choice, and one's ideas about ultimate use-access convenience. For examples, the wipe(s) may be arranged in a thin stack either (1) in front (as is specifically illustrated here in the drawings), (2) in back of the folded bag, (3) within the folds of the bag, or (4) even within the inside of the bag itself.

Preferably, the lateral dimensions of pocket 26 (see especially FIGS. 1, 3 and 4), which dimensions are completely a matter of free choice at the discretion of the invention practicer, are proportioned somewhat as shown in the herein accompanying drawings. The resulting, stored-contents thickness of the pocket will, of course, depend upon the added thicknesses of the combined (a) folded bag 28, and (b) the chosen count of included clean-up wipes. Here, too, proportioning of this dimension in relation to the dimensions of other parts of the overall diaper structure is probably best when it is like that generally shown in FIG. 2 in the drawings. These various dimensional and proportioning considerations are, of course, relevant to controlling overall diaper size/bulk, and are, as suggested just above, freely determinable by the party practicing this invention.

Further regarding pocket structure, or pocket, 26, per se, while this structure may be constructed as a fully complete pocket unit, i.e., a unit with appropriately edge-united front and back sides, the entirety of which unit becomes attached/integrated with the front outside of a diaper body 22 as shown herein, in the preferred embodiment of the invention which is now being described, and which is illustrated in the drawings, pocket 26 is conveniently formed with just a front, panel-like side, or panel, 26*b* whose opposite side and base lateral edges are suitably bonded to the front outer portion 22*c* of diaper body 22 pocket as seen in FIGS. 1 and 3.

Soilage-imperviousness for the pocket comes from both the conventional material employed on the outer side 22*a* in body 22, and an appropriately chosen, soilage-impervious, typically plastic material selected to form the front-panel part of the pocket. Bonding of this singular pocket front-panel side to the diaper body may be accomplished through any appropriate, conventional bonding technique—not part of the present invention.

Bag 28 which, as has been mentioned earlier, is preferably formed of any suitable, lightweight plastic material, has the usual closed-end 28*a* (see FIGS. 7, 11 and 12) appropriately, and in any conventional manner, attached/anchored, and thereby unitized with main-body structure 22, (a) beneath pocket-closure flap 26*c* directly adjacent the previously described pocket's upper-end exposure opening (as represented schematically, and somewhat differently, in each of FIGS. 1 and 2), (b) at but a single attachment location, or point, 36 in the overall diaper, and (c) just (i.e., only) to the diaper's main body 22 right at the upper side of previously described region 26*a*. The normally and nominally open end of bag 28 is shown in different diaper-change stages at 28*b* in FIGS. 7-12, inclusive. As can be seen particularly well in FIGS. 1 and 3 in the drawings, in what has been referred to hereinabove as a pre-diaper-change condition of diaper 20, bag 28 is arranged in a manner whereby that portion of it which lies between its closed and open ends extends inwardly into pocket 26 relative to anchoring location 36 and the upper-end exposure opening for the pocket.

Bag 28, as outlined earlier, is deployable from the location of singular attachment 36 outwardly relative to diaper body 22 so as to be employable ultimately as a unitized disposal container for all soiled diaper-associated structure.

Turning attention now to FIGS. 5-12, inclusive, and discussing them in progressive numeric order, as was mentioned and explained earlier, particularly with reference to the specific descriptions set forth above in this text regarding the contents of these several drawing figures, these eight figures illustrate a typical baby clean-up and diaper-change activity involving use of the soilage-management structure of the present invention. I understand that there are many different baby clean-up and diaper-change practices/sequences, etc., that parents and other caregivers employ with respect to changing a baby's diaper, and I have simply chosen one fairly typical such sequence for illustrating the practice and utility of the present invention. In the sequence which now follows describing this practice, there is an assumption made that it is a parent who is performing the clean-up and diaper-change activities.

In FIG. 5, pictured (fragmentarily) is a baby in a soiled diaper which is ready for removal to enable baby clean-up and diaper change, all in preparation for soiled-diaper-componentry management and eventual soiled-componentry disposal, in accordance with the present invention.

FIG. 6, helpfully aided by a small arrow 38, shows opening by the baby's parent (or caregiver) of the upper-end exposure opening of pocket 26, and initial hand deploying of disposal bag 28 whose closed and anchored end 28*a* remains solidly affixed just to the diaper's main body directly adjacent the pocket's upper-end exposure opening.

In FIG. 7, which shows a slightly later stage in the process now being described, and which is helpfully aided by a collection of several arrows 40 42, 44, 46, bag 28, with its open end 28 fully exposed, has been essentially fully deployed from pocket 26, the three pocket-contained clean-up wipes 30, 32, 34 have been removed in preparation for use, and the right side (in this figure) of diaper 20 has been released from closure around the baby in preparation for removal of the soiled diaper.

In FIG. 8, the soiled diaper has been completely released from enclosure of the baby and has been opened up, and wipe 30 is shown being used in the mode of baby clean-up.

FIG. 9, illustrates a further stage of soilage management according to the invention, with a plurality of arrows 48, 50, 52, 54 enhancing illustrations of (a) the parent placing the now used and soiled clean-up wipes against the inside of the soiled diaper main body, and (b) the beginning process of the parent's crumpling, folding and otherwise gathering all of these soiled materials ultimately into a somewhat tightened ball-like configuration, such as that shown generally at 56 in FIG. 10, in preparation for a next-stage of this soiled-component configuration insertion into deployed disposal bag 28.

FIG. 10, with the aid of three arrows 58, 60, 62, demonstrates initial full opening up of the open end 28*b* in disposal bag 28, and reversal, or turning back of the bag upon itself, in what may be referred to as an inside-out fashion, to receive and thereby collect the soiled-componentry ball 56.

FIG. 11 illustrates that this inside-out reversal, soiled-componentry collection and containment process is now essentially completed, with bag 28 now readied to be closed, typically and conveniently as by knotting, thereby sealing its contents inside to create, as seen in final FIG. 12, a completed containment operation using the soilage management structure of the present invention to finish with what is referred to herein as a singular disposable unit 64 ready for clean-handling, appropriate discard.

It should thus be very apparent how the unitary, integrated diaper of this invention, with its unique, included, readily-employable soilage-management structure, linked specially, and very compactly, to otherwise conventional main-body diaper structure, advances the art of disposable diapers.

In its preferred embodiment, the diaper of the present invention, in addition to possessing a diaper-body-attached/unitized, deployable disposal container structure in the form of a lightweight, soilage impervious bag anchored adjacent its closed end to the diaper body (as described above), designed for containing, following baby clean-up, all soiled, diaper-associated components for easy discard as a singular disposable unit, it includes at least one baby-clean-up wipe (and most preferably more than one). Accordingly, the invented diaper offers an extremely convenient, quickly and cleanly handleable, effectively "all-in-one" disposable-diaper package eliminating the need to deal with separately packaged components that are regularly, routinely, and usually frequently, needed for fully managing soiled-diaper baby clean-up.

Several practical, and in some cases user-desirable, modifications of the preferred diaper construction have been mentioned herein, and it will be evident that each of these modification, as well as the preferred diaper construction, per se, are readily incorporable, with little or no appreciable modification in basic disposable-diaper-fabrication techniques, in what is otherwise today conventional, principal-form, disposable diaper construction.

I certainly appreciate that still-to-be-thought-of variations and modifications that are other than those set forth above are possible, and may well come to the minds of disposable diaper designers and users, and it is my intention that all such other variations and modifications will be recognized as coming within the claimed spirit of this invention.

I claim:

1. A unitary, disposable diaper comprising
main body structure having an outer side possessing a front portion, and
integrated soilage-management structure disposed on said front portion and including
  (a) an initially closed, but selectively openable, soilage-impervious pocket structure (a) formed collaboratively by a region in said front portion and an independent, continuous, front panel component having four, perimetral edges only three of which are joined to said front portion, (b) having an upper, elongate openable end defined by the front portion's unjoined edge, and (c) possessing a lateral dimension which substantially defines both the effective width of the pocket structure and the length of said openable end, said openable end being nominally closed by a slender, independent-component, substantially full-pocket-width closure flap which is manipulable to expose the openable end for access to the inside of the pocket structure, and
  (b) initially stored in said pocket structure, an ultimately closeable and sealable, soilage-impervious disposal bag structure having normally open and normally closed ends, deployable from the pocket structure, and thereafter employable to form a soilage-impervious disposal container, said bag structure being attached, in the overall diaper, solely to said main body structure, and at a single attachment point which exists between the bag structure's normally closed end and a location on the main body structure which is immediately adjacent the pocket structure's openable end.

2. A unitary, disposable diaper comprising
main body structure having an outer side possessing a front portion, and
integrated with said main body structure, soilage-management structure including
  (1) soilage-impervious pocket structure formed by
    (a) a region in said front portion possessing elongate upper, lower, and lateral sides,
    (b) substantially coextensive with said region, a confronting and spaced front panel having a plurality of elongate perimetral edges, including (i) a pair of lateral edges, (ii) a base edge, and (iii) an upper free edge which is spaced from said front portion and its said region, said panel being continuous between its said edges, said lateral and base edges being joined along their respective lengths, respectively, to said lateral and lower sides of said region, and said upper free edge being free along substantially its entire length, specifically lacking any joinder therealong to said front portion and the upper side of its said region, said upper free edge, together with the spaced and confronting upper side of said region, defining an elongate exposure opening for the pocket structure that extends substantially the full width of the pocket structure along substantially the entire respective lengths of each of said upper free edge of said panel and said upper side of said region, said exposure opening accommodating access to the pocket structure's inside which is defined by the space existing between said panel and said region, and (c), nominally, but openably, closing said exposure opening, in a pre-diaper-change condition of the diaper, an independent-component, elongate, slender closure flap having a length substantially matching those of said upper free edge of said panel and said upper side of said region, said flap being joined along its length to said front portion along said region's said upper side, and immediately adjacent said panel's said free upper edge, selectively manipulable to open said exposure opening at an appropriate time during a diaper-change procedure to expose the inside of the pocket structure for access, and (2) initially stored in said pocket structure, an ultimately closeable and sealable, soilage-impervious disposal bag structure having open and closed ends, attached, only at its said closed end, and through a singular attachment, solely to said main body structure so as to function as a unit therewith, said singular attachment being disposed at a location which is positioned immediately adjacent the pocket structure's said exposure opening, said bag stricture, in the mentioned pre-diaper-change condition of the diaper, being arranged, relative to said pocket structure, in a manner whereby that portion of the bag structure which lies between its closed and open ends extending inwardly into the pocket structure relative to the pocket structure's exposure opening, said bag structure being deployable from the location of said singular attachment outwardly relative to said main body structure so as to be employable, in the performance of a diaper-change procedure, as a soilage-impervious disposal container for receiving and sealing, as a whole, all soiled diaper-associated structure in a contained and sealed condition readied for disposal as a disposable unit.

* * * * *